United States Patent [19]
Nilsson

[11] Patent Number: 5,882,902
[45] Date of Patent: Mar. 16, 1999

[54] AMINO ACID CONJUGATE

[75] Inventor: Kurt Nilsson, Lund, Sweden

[73] Assignee: Bioflexin AB, Lund, Sweden

[21] Appl. No.: 793,876

[22] PCT Filed: Sep. 6, 1995

[86] PCT No.: PCT/IB95/00740

§ 371 Date: May 12, 1997

§ 102(e) Date: May 12, 1997

[87] PCT Pub. No.: WO96/07753

PCT Pub. Date: Mar. 14, 1996

[30] Foreign Application Priority Data

Sep. 6, 1994 [SE] Sweden .................................. 9403011
Jun. 10, 1995 [SE] Sweden .................................. 9502159

[51] Int. Cl.$^6$ ............................ C12P 19/44; C12P 19/26; C12P 19/64
[52] U.S. Cl. ................................ 435/74; 435/73; 435/84; 435/193; 536/1.11; 536/4.1; 536/18.7
[58] Field of Search .................................. 536/1.11, 4.1, 536/18.7; 435/73, 74, 193, 84

[56] References Cited

U.S. PATENT DOCUMENTS 5,583,042 12/1996 Roth .......................................... 435/84

OTHER PUBLICATIONS

APS Abstract JP409037790A (Feb. 10, 1997) Ajisaka et al.

*Primary Examiner*—Herbert J. Lilling
*Attorney, Agent, or Firm*—Bevridge, Degrandi Weilacher & Young, L.L.P.

[57] ABSTRACT

Method for synthesis of GalNAcα-serine or GalNAcα-threonine containing compounds, including at least one reaction where an α-saccharide or α-glycoside of GalNAca is used as gylcosyl donor and a derivative of serine of threonine is used as acceptor in a transglycosylation reaction with N-acetyl-α-D-galactosaminidase as the catalyst, wherein said acceptor has been modified in its N-terminal α-amino group and optionally in its c-terminal carboxyl group.

9 Claims, No Drawings

AMINO ACID CONJUGATE

The present invention describes a new method to produce O-glycosylated amino acids, O-glycosylated peptides or derivatives of these. In a further aspect the present invention relates to products produced by the above method as well as uses of the resulting products.

Glycoconjugates contain oligosaccharide chains with up to twenty monosaccharide units and several sequences have been shown to have biological activity e.g. in the binding to different cells, pathogens, toxins, antibodies or other proteins on cell surfaces, in cancer metastasis, in inflammation processes (for example selectin-carbohydrate interactions), binding of white blood cells to the blood vessel wall, as a modifier of the activity, stability and biological activity of proteins, and as immunogenic substances which have potential for vaccination against different diseases. An extensive literature has been developed during the last few years in this field and there are several review articles on this type of biology, glycobiology, e.g. in Annual Review of Biochemistry and in current opinion in Structural Biology (see for example volume 3, 1993) incorporated herein by reference.

One type of glycoconjugate, the glycoproteins, contain carbohydrate-peptide sequences in which the carbohydrate unit is bound to the peptide or protein chain via mainly three different types of linkages, the O-glycosidic linkage represented by GalNAcα-OSer and GalNAcα-OThr, that is the linkage between N-acetyl-D-galactosamine and the hydroxyl group on a L-serine or a L-threonine residue in the peptide of protein chain (several such linkages can be found in a peptide or protein chain depending on the number of serine or threonine units in the molecule), the N-glycosidic linkage between N-acetyl-D-glucosamine and the amide function in asparagine, GlcNAcβ-N-Asn, and the O-glycosidic linkage between galactose or xylose and different hydroxyl group containing amino acids. Recently, also the β-O-glycosidic linkage between N-acetyl-D-glucosamine and the hydroxyl group on serine or threonine, abbreviated GlcNAcβ-OSer and GlcNAcβ-OThr, respectively, has been of increased interest, e.g. because of its suggested importance in the DNA-replication in the nucleus of eucaryotic cells.

These types of linkage are of interest to produce by synthetic methods for fundamental studies and for synthesis of biologically or pharmaceutically active fragments of glycoproteins, for instance for use as vaccines or therapeutics. It is also important to be able to synthesize analogs or derivatives of the structures above for example with other types of sugar and/or configuration, as e.g. mannosamine and the α- or β-configuration to modify or to increase the biological activity of the conjugate.

Several of these conjugates have earlier been synthesized by chemical or enzymatic methods. The disadvantages with chemical synthesis is that several reaction steps are required with extension protection group chemistry to obtain stereo- and regioselective synthesis of the conjugate and often, as a side reaction, β-elimination and racemization of the amino acid residue is obtained due to the weakly acidic nature of the optically active C—H linkage. The stereospecific preparation of GalNAcα-OSer, GalNAcα-OThr and derivatives of these structures is especially difficult to achieve with chemical methods.

This invention describes a novel method based on enzymatic synthesis for the preparation of such GalNAcα-linked compounds.

Enzymatic synthesis of glycosidic linkages can be carried out with glycosyltransferases (EC 2.4) and with glycosidases (EC 3.2) (see e.g. K. Nilsson, Trends in Biotechnology, 1988, pages 256–264, incorporated herein). Glycosyltransferases are in general not available in quantity for large-scale synthesis, have a high acceptor specificity which limits the efficiency with unnatural or modified acceptors and are dependent on nucleotide sugars as glycosyl donors. Glycosidases are abundant and have been used for synthesis of non-modified GalNAcα-Ser e.g. employing the substrates GalNAc and L-serine in high concentration, i.e. employing conditions for reversed hydrolysis (equilibrium) reactions (Johanson et al, Enzyme Microb. Technol., 13, 781, 1991). The yield in this reaction is however relatively low (ca. 5% according to HPLC), high concentration of purified enzyme (N-acetyl-α-D-galactosaminidase) is required, the reaction is relatively slow and N-glycosylation of the anomeric carbon of the GalNAc unit is a severe side reaction.

One purpose of the present invention is to minimize the above mentioned problems in the chemical or enzymatic synthesis of compounds containing the GalNAcα-Serine and GalNAcα-Threonine or GlcNAcβ-Serine and GlcNAcβ-Threonine structures. The method according to the invention involves at least one reaction where an α-glycoside of a saccharide which contains GalNAc at the reducing end (D-GalNAcα-R in the scheme below) is used as glycosyl donor and a derivative of serine or threonine (HSer-R' and HThr-R' in the scheme below) is used as acceptor in a transglycosylation reaction with an endo- or exo-N-acetyl-α-D-galactosaminidase (GalNAc:ase below) as the catalyst, or, alternatively, where a β-glycoside of a saccharide which contains GlcNAc at the reducing end (D-GlcNAcβ-R in the scheme below) is used as glycosyl donor and a derivative of serine or threonine (HSer-R' and HThr-R' in the scheme below) is used as acceptor in a transglycosylation reaction with an endo- or exo-N-acetyl-β-D-glucosaminidase (GlcNAc:ase below) as the catalyst (scheme 1):

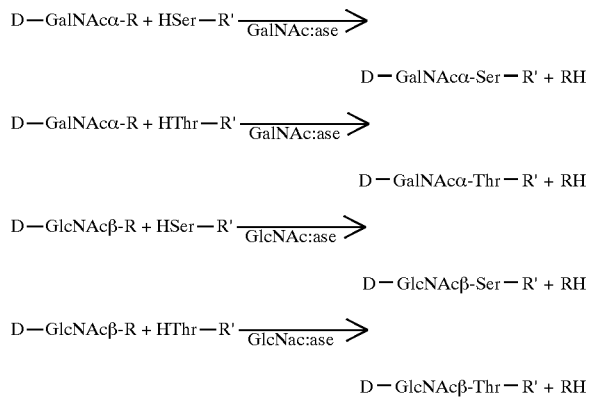

where D represents a hydroxyl group on GalNAc or GlcNAc (in the case of exo-N-acetyl-α-D-galactosaminidase or exo-N-acetyl-β-D-glucosaminidase) or an inorganic or organic group, for example a saccharide group (in the latter case an endo-glycosidase is used as the catalyst); R represents a glycosidically bound aglycon (e.g., inorganic or organic group such as a glycosidically bound F-, alkyloxy- or aryloxy group) and HSer-R' and HThr-R' represent the modified serine or threonine acceptor. Examples of acceptors are L- or D-serine or L- or D-threonine containing compounds or peptides which have been modified in the N-terminal with an organic group (e.g., R—C(O) or R—O—C(O)— groups, such as for example formyl, acetyl, allyloxycarbonyl (Alloc), t-butyloxycarbonyl (Boc), benzyloxycarbonyl, fenacetyl-, 4-metoxybenzyloxycarbonyl- (Moz-), or 9-fluorenyl methyloxycarbonyl (Fmoc) groups) and which optionally also have been modified in the carboxyl terminal with an alkoxy or aryloxy group (e.g., methoxy, ethyloxy or phenoxy group) forming an ester group at the C-terminal group. For synthesis of protection group modified amino acids or peptides see Houben-Weyl, Bd 15/1, Kontakte 3/79, 14 and especially Synthetic Peptides, G. A. Grant, Editor, W. H. Freeman and Company, New York, 1992 (both of which are incorporated by reference in their entirety) and references therein. If a peptide derivative is acceptor in the reaction according to the invention, the size is preferably di- to penta peptide but even bigger peptide fragments can be glycosylated according to the invention. As acceptor there can also be used amino acid/peptide derivatives in the D-configuration or a mixture of D and L-configuration.

In one embodiment, the method according to the invention involves at least one reaction where an α-glycoside of GalNAc (GalNAcα-R in the scheme below) is used as glycosyl donor and a derivative of Serine or Threonine (HSer-$R^1R^2$ and HThr-$R^1R^2$ in the scheme below) is used as acceptor in a transglycosylation reaction with exo-N-acetyl-α-D-galactosaminidase (GalNAc:ase below) as the catalyst (scheme 1):

GalNAcα-R + HSer—$R^1R^2$ $\xrightarrow{\text{GalNAc:ase}}$

GalNacα-Ser—$R^1R^2$ + RH

GalNAcα-R + HThr—$R^1R^2$ $\xrightarrow{\text{GalNAc:ase}}$

GalNacα-Thr—$R^1R^2$ + RH where GalNAcα-R represents compounds of the type shown below:

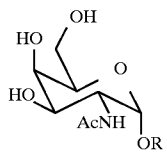

where R is an aliphatic or aromatic compound (e.g. phenyl or nitrophenyl group):

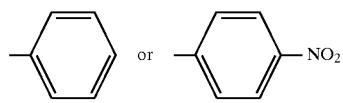

H-Ser-$R^1R^2$ and H-Thr-$R^1R^2$ in scheme 1 above represent molecules of the type shown below:

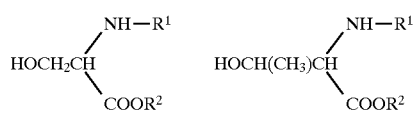

where $R^1$ represents a protecting group on the amino group and $R^2$ represents a protecting group on the carboxyl group. $R^1$ is preferentially selected from acyl or alkyloxy groups such as acetyl, allyloxy and butyloxy groups, respectively, and $R^2$ is preferentially selected from alkyl or aryl groups such as methyl, ethyl or phenyl groups; optionally, the carboxyl group is unprotected but preferably is protected.

Typical examples of H-Ser-$R^1R^2$ acceptor compounds used in the method according to the invention are thus:

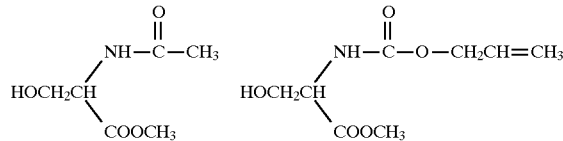

GalNAcα-Ser-$R^1R^2$ and GalNAcα-Thr-$R^1R^2$ compounds produced according to scheme 1 are thus:

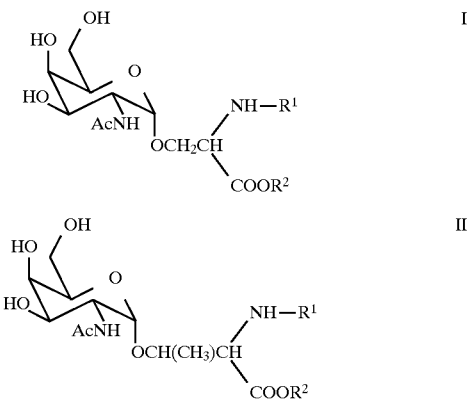

Typical example of GalNAcα-Ser-$R^1R^2$ compounds produced according to scheme 1 are thus:

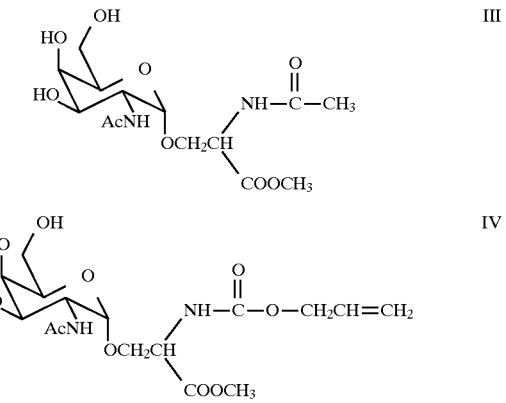

The reactions conditions are not limiting but are selected with regard to the specific reaction and source of enzyme. For example, the pH is often selected in the range of 4–8, the reaction temperature in the range −20° to 70° C., the predominant solvent can be water with buffer salts (e.g., phosphate, acetate, citrate, carbonate and others known in the art), organic solvent (e.g., acetone, acetonitrile and others known in the art) or mixed solvents, e.g. mixed water-organic solvent or two-phase systems. The reaction can be followed by, traditional methods (such as TLC, HPLC, absorbance measurements e.g. of released phenol or nitrophenol from donor), and the reaction is preferentially terminated at the optimal product yield. The method for purification is not limiting and may include any of extraction, precipitation, column chromatography (with e.g., silica, Sephadex, active carbon, ion exchanger as solid phase).

The product can for example be purified by mild acidification (pH 4–5) followed by extraction with suitable organic solvent (e.g. ethyl acetate) to remove unreacted acceptor, followed by for example column chromatography or continued extraction with a less unpolar solvent to remove the product into the organic phase, or evaporation alternatively freeze drying of the water phase followed by extraction with for example methanol column chromatography of the methanol phase.

The enzyme may be used in immobilized, cross-linked or in soluble form and in a more or less purified form. When immobilized, the enzyme may be used adsorbed to a solid phase (e.g. a glass, silica, polystyrene, another plastic, a polysaccharide (e.g. cellulose or agarose)) or enriched in a water phase in a two-phase system. Examples are the use of enzyme adsorbed to e.g. celite or $XAD^R$ resins. The latter may be especially useful in the cases when organic solvents (acetone, acetonitrile, tetrahydrofurane) are used as cosolvents (in high concentrations e.g. >70%) or in two-phase systems. The enzymes may be obtained from natural sources or from recombinant cells.

In a specific embodiment, the method according to the invention also involves the use of chemical or enzymatic methods for specific modification of the product with organic or inorganic groups or for the specific removal of protection groups on the amino and/or carboxyl groups. In general, protection groups are removed according to standard chemical techniques known to those skilled in the art. in addition, enzymes can be used. Thus, for example lipase or protease may be used according to the invention for removal of the $R^2$ group producing product with a free carboxyl group, e.g. reaction of compounds III and IV above with lipase gives V and VI below:

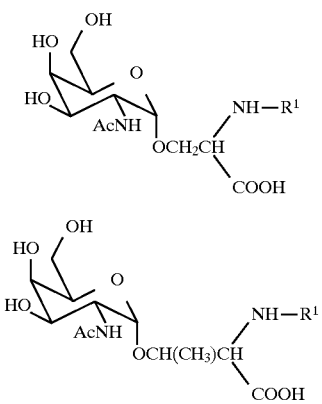

Such compounds are useful for binding to other molecules via the carboxyl group, e.g. for preparation of glycopeptides using peptide forming enzymes such a proteases or using standard chemical techniques for peptide formation (such as carbodiimide reagents).

As an additional example, to remove the methyl ester group to obtain the product of type V, the methyl ester containing product III (350 mg) was dissolved in sodium phosphate buffer (pH 7, 50 mM, 14 ml) and 700 mg of the lipase (Boehringer, Chirazyme L-7; 2 g) was added. The reaction was allowed to proceed at 45° C. for 5 days and the product purified by column chromatography (Sephadex G10 and silica) which gave 164 mg of freeze-dried product).

The amino group of the product of scheme 1 may also be deprotected and then used for various purposes such as in various peptide forming reactions employing peptide forming enzymes or chemical methods. When chemical methods are used for peptide formation the hydroxyl groups of the sugar may first be protected e.g. with acyl groups. See for example Houben-Weyl, Bd15/1 Kontakte 3/79, 14 and especially Synthetic Peptide, G. A. Grant, Editor, W. H. Freeman and Company, New York, 1992 for reviews on peptides and glycopeptides).

GalNAcα-Ser or GalNAcα-Thr containing compounds thus prepared are useful for e.g. binding to solid phases equipped with a covalently bound spacer molecule, e.g. a covalently bound alkyl amine residue such as hexylamine or covalently bound alkyl. carboxyl acid such as covalently bound mercaptopropionic acid, e.g. as bound to soluble or insoluble polymers or to other surfaces, to which compounds e.g. of the type V and VI can be covalently bound with standard peptide forming reactions between the amino group of the hexylamine residue and the carboxyl group of the GalNAcα-Ser or GalNAcα-Thr compound or between the solid phase carboxyl group and the amino group of said compounds. Alternatively, the GalNAcα-Ser or the GalNAcα-Thr compound is first modified in solution with the spacer molecule and the resulting spacer modified compound is then used for binding to the solid phase (or alternatively to a protein, peptide, lipid, polyethylene glycol or other organic molecule of interest for the specific application).

The solid phase thus prepared containing bound GalNAcα-Ser or GalNAcα-Thr containing residues can be used for analytical, down stream processing (affinity chromatography) or for (solid phase) synthetic purposes. Example of solid phases are those based on synthetic or naturally occurring polymers, such as polystyrene, polyacrylamine, copolymers, etc, cellulose, agarose, etc. commonly used in analytical or down stream processing applications, metal coated surfaces, such as gold or silver coated materials and colloidal gold particles. Methods for binding of molecules to such surfaces are well documented in the literature, (see e.g. Method in Enzymology, vol. 44, 104, 134–137 and in PCT/SE94/00343) and are straightforward to apply in analytical, down stream processing or solid phase synthetic applications.

The GalNAcα-Ser or GalNAcα-Thr containing compounds obtained in the scheme 1 and/or after immobilization with the methods above are useful e.g. as acceptors in enzymatic reactions employing either glycosyltransferases or glycosidases as catalysts. Thus, by using a glycosidase specific for the glycosyl donor Don-R (where Don symbolizes a sugar unit and R symbolizes an aglycon such as a nitrophenyl group, which is bound in α- or β- configuration to the sugar group) one can obtain the product Don-GalNAcα-Ser-R" or Don-GalNAcα-Thr-R" (where R" symbolize either -H, i.e. no modification on the serine or threonine residue, or a modification by an amino acid, peptide or other organic group, on at least one of the amino or carboxyl groups):

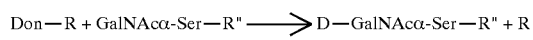

Don above may be selected from the group consisting of compounds containing at lest one L-fucosyl, D-glucosyl-, D-galatosyl-, D-mannosyl, D-xylosyl, N-acetyl-D-glucosaminyl, N-acetyl-D-galactosylaminyl or sialyl group. The glycosidase may be selected from the group of exo- or endoglycosidases belonging to the EC 3.2. class of hydrolases.

An example is the use of β-galactosidase preparation (obtained from e.g. bovine testes) as catalyst and lactose or Galβ-PNP (PNP=p-nitrophenyl) as glycosyl donor to prepare Galβ1-3GalNAcα-Ser-R" or Galβ1-3GalNAcα-Thr-R", by carrying out the reaction in e.g. sodium acetate or sodium phosphate buffer with or without organic solvents, and at room temperature or at elevated temperature.

With glycosyltransferases a nucleotide sugar, Don-N, is used as donor and GalNAcα-Ser-R" or GalNAcα-Thr-R" as acceptor. An example is the use of sialytransferase to produce NeuAcα2-6GalNAcα-Ser-R" or NeuAcα2-6GalNAcα-Thr-R" employing CMP-NeuAc as donor. Glycosyltranferases are also of interest for use with solid phase bound GalNAcα-Ser-R" or GalNAcα-Thr-R".

The above types of disaccharide products can be applied for analytical down-stream processing, or (solid phase) chemical or enzymatic synthetic purposes as described above.

The products are also of interest for therapeutic applications, for modification of organic compounds of therapeutic interest, or of interest as food or cosmetical product additives to obtain products with novel properties.

Previous preparative enzymatic synthesis of GalNAc-Ser or GalNAc-Thr relies on large quantities of expensive GalNAc as glycosyl donor in comparably slow equilibrium reactions affording low yields, requiring high concentrations of purified enzyme, and which give side products as N-glycosylation of GalNAc which is difficult to separate from the O-glycosylated GalNAc-Serine or Threonine products. With the method according to the present invention, higher yields (in the range 10–50% or higher) are obtained, much less enzyme is require due to more reactive donor substrate, the enzyme does not need extensive purification before use in the synthesis according to the invention and N-glycosylation is avoided.

The yield of product is often in the range of 10–50% as calculated on the donor. Depending on the amount of enzyme activity added (Units of enzyme), the reaction can be carried out for e.g. 15 minutes up to 24 hours or more. In general, the reaction time is determined by the reaction rate and is stopped when the donor is consumed (if this is used as the limiting substrate) or preferably when the maximum amount of product has been formed (as determined e.g. by HPLC). Non-limiting examples of reaction according to scheme 1 above is given below.

EXAMPLES

Compounds of the type III, IV, and V were prepared by reaction of GalNAcα-PNP (typically added to a concentration in the range 50–150 mM) with either of Ac-N-L-Ser-OMe or Alloc-N-L-Ser-OMe, respectively, as acceptors (in a typical concentration in the range 150 mM–2M) suspended in sodium acetate buffer, pH 4.4, and enzyme was added (enzyme used in crude form as obtained from *Aspergillus oryzae* by ammonium sulphate fractionation of a commercial (Sigma, St. Louis, Mo.) β-galactosidase preparation (1:50% ammonium sulphate precipitation; 2:80% ammonium sulphate precipitation followed by dialysis and freeze-drying). Typically the reaction was carried out at a given temperature in the range room temperature to 45° C., until the main part of the glycosyl donor had reacted. The product (III and IV, respectively) was purified by separation on a column packed with e.g. Sephadex G10 (Pharmacia, Uppsala, Sweden; water as eluent), after which product containing fractions were freeze-dried. To remove the methyl ester group the product treated with lipase (e.g. Boehringer, Chirazyme®L-7) which gave product of type V after separation on e.g. ion-exchanger (Q-Sepharose, Pharmacia, Uppsala, Sweden). Compounds of type V and VI were prepared similarly employing the corresponding threonine acceptors.

GalNAcα-PNP (170 mM) and N-Alloc-L-Ser-OMe (0.9M) suspended in sodium acetate buffer (pH 4.4) were reacted at 45° C. for 4 hours with 30 mg (per 0.5 ml reaction volume) of freeze-dried GalNAcα-ase as catalyst (prepared as described above). At this time the reaction was stopped indicating formation of 40 mM product (HPLC; ca 23% molar yield as calculated on reacted donor).

GalNAcα-PNP (170 mM) and N-acetyl-L-Ser-OMe (2M) suspended in sodium acetate buffer (pH 4.4) were reacted as described above at 45° C. with freeze-dried GalNAcα-ase as catalyst (prepared as described above) until ca 70 mM product was obtained (HPLC; ca 40% molar yield as calculated on reacted donor). GalNAcα-PNP (170 mM) and N-acetyl-L-Thr-OMe (0.9M) suspended in sodium acetate buffer (pH 4.4) were reacted as described above at 45° C. with freeze-dried GalNAcα-ase as catalyst (prepared as described above) until ca 49 mM product as obtained (HPLC; ca 29% molar yield as calculated on reacted donor).

Further variations and modifications of the foregoing will be apparent to those skilled in the art and such variations and modifications are attended to be encompassed by the claims that are appended hereto.

Swedish Priority Application 9403011-1 filed on 6 Sep. 1994 and 9502159-8 filed on 10 Jun. 1995 are relied on and incorporated by reference in their entirety. Furthermore, Swedish Application 9304316-4 filed on 24 Dec. 24 1993 and PCT Application PCT/IB94/00444 filed on 27 Dec. 1994 are relied on and incorporated by reference.

I claim:

1. Method for synthesis of GalNAcα-serine or GalNAcα-threonine containing compounds, comprising at least one reaction where an α-saccharide or α-glycoside of GalNAc is used as glycosyl donor and a derivative of serine or threonine is used as acceptor in a transglycosylation reaction with N-acetyl-α-D-galactosaminidase as the catalyst, wherein said acceptor has been modified in its N-terminal α-amino group and optionally in its C-terminal carboxyl group.

2. A method for the synthesis of a GalNAcα-serine or GalNAcα-threonine containing compound, said method comprising reacting (a) a glycosyl donor which is α-saccharide or α-glycoside of GalNAc, (b) an acceptor which is serine or threonine or peptide containing serine or threonine wherein said serine or threonine contains a protection group in its N-terminal α-amino group and optionally i its C-terminal carboxyl group, and (c) an enzyme which is N-acetyl-α-D-galactosaminidase.

3. The method according to claim 2, further comprising isolating the product from the reaction mixture.

4. The method according to claim 2, wherein said protection group in said N-terminal α-amino group is an acyl or alkyloxy group and wherein said protection in said C-terminal carboxyl group is an alkyl or aryl group.

5. The method according to claim 2, further comprising subsequently removing said protection group in said N-terminal α-amino group and/or said protection in said C-terminal carboxyl group.

6. The method according to claim 2, further comprising using said GalNAcα-serine or GalNAcα-threonine containing compound as an acceptor in a reaction with a glycosyltransferase or glycosidase and glycosyl donor Don-R where Don symbolizes a sugar unit and R symbolizes an aglycon which is bound in α- or β- configuration to said sugar group.

7. Method for synthesis of GalNAcα-serine or GalNAcα-threonine containing compounds, comprising at least one reaction where an α-saccharide or α-glycoside of GalNAc or β-saccharide or α-glycoside of GlcNAc is used as glycosyl donor and a derivative of serine or threonine is used as acceptor in a transglycosylation reaction with an endo- or exo-N-acetyl-α-D-galactosaminidase or an endo- or exo-N-acetyl-β-D-glucosaminidase as the catalyst, wherein said acceptor has been modified in its N-terminal α-amino group and optionally in its C-terminal carboxyl group.

8. A method for the synthesis of a GalNAcα-serine or GalNAcα-threonine containing compound, said method comprising reacting (a) a glycosyl donor which is α-saccharide or α-glycoside of GalNAc or β-saccharide or α-glycoside of GlcNAc, (b) an acceptor which is serine or threonine or peptide containing serine or threonine wherein said serine or threonine contains a protection group in its N-terminal α-amino group and optionally in its C-terminal carboxyl group, and (c) an enzyme which an endo- or exo-N-acetyl-α-D-galactosaminidase or an endo- or exo-N-acetyl-β-D-glucosaminidase.

9. The method according to claim 8, further comprising isolating the product from the reaction mixture.

* * * * *